United States Patent [19]

Nomura et al.

[11] Patent Number: 5,080,741

[45] Date of Patent: Jan. 14, 1992

[54] METHOD FOR MANUFACTURING DISPOSABLE GARMENTS

[75] Inventors: Hironori Nomura, Iyomishima; Taiji Shimakawa; Yoshinori Matsura, both of Kanonji; Hiroki Yamamoto, Kawanoe; Hirofumi Ohnishi, Iyomishima, all of Japan

[73] Assignee: Uni-Charm Corporation, Ehime, Japan

[21] Appl. No.: 581,573

[22] Filed: Sep. 12, 1990

[30] Foreign Application Priority Data

| Sep. 13, 1989 | [JP] | Japan | 1-238943 |
| Sep. 21, 1989 | [JP] | Japan | 1-245432 |
| Sep. 22, 1989 | [JP] | Japan | 1-247686 |
| Sep. 26, 1989 | [JP] | Japan | 1-249768 |
| Oct. 5, 1989 | [JP] | Japan | 1-261838 |

[51] Int. Cl.$^5$ ............................................. B31F 1/00
[52] U.S. Cl. .................................. 156/201; 156/226; 156/552; 156/204; 604/358

[58] Field of Search .............. 156/256, 204, 206, 62.2, 156/249, 438, 461, 519, 556, 554, 270, 205, 226, 227, 200, 201, 202, 552, 464, 467; 604/358, 373, 385.1, 385.2

[56] References Cited

U.S. PATENT DOCUMENTS 4,409,052 10/1983 von Agris et al. ................. 156/227

Primary Examiner—David A. Simmons
Assistant Examiner—Robert Barker
Attorney, Agent, or Firm—Fred Philpitt

[57] ABSTRACT

Inner members formed by attaching absorbent cores to inner webs longitudinally thereof with predetermined spaces between the cores are folded on themselves along their center lines so that the cores partially lie on a first outer surface and partially lie on a second outer surface opposed to the first outer surface. A pair of continuous outer webs having widths to cover the first and second outer surfaces are provided with elastic members for leg-openings and waist-openings, and attached respectively to the first and second surfaces to form a continuous laminate. Successively the laminate is sealed and cut at predetermined areas, and individual disposable garments are produced.

6 Claims, 5 Drawing Sheets

METHOD FOR MANUFACTURING DISPOSABLE GARMENTS

BACKGROUND OF THE INVENTION

The present invention relates to a method for manufacturing disposable garments such as training underpants for infant, incontinence underpants and so-called sanitary underpants.

It is well known, for example, from the techniques as disclosed in Japanese Patent Application Disclosure Gazettes Nos. 1982-77304 and 1982-117602 to form such garments by providing at least one of respective single continuous inner and outer webs with elastic members for leg-openings and for a waist-opening, intermittently placing absorbent cores between said inner and outer webs longitudinally thereof so as to form a continuous laminate and cutting said laminate transversely thereof along predetermined lines.

According to the conventional methods for manufacturing such articles inclusive of the above-identified prior art, a continuous laminate is folded in two and then heat sealed along the locations corresponding to lateral side edges of individual articles as put on users, in order to form front and rear bodies of the individual articles.

With the above-mentioned prior art, however, it has been difficult to fold the continuous laminate in a neat manner even though the folding is performed as the continuous laminate is being kept taut, because the continuous laminate to be folded in two includes the elastic members for the leg-openings and for the waist-opening which are ready to contract. In other words, the individual articles are susceptible to partial floating, development of wrinkles and misalignment of front and rear bodies while the laminate is heat sealed. As a result the individual articles tend to have less neat appearance.

It is an object of the present invention to provide a method for manufacturing disposable garments wherein outer webs are provided with elastic members for the leg-openings as well as for the waist-opening, on one hand, and inner members having inner webs and cores are folded in two, on the other hand, and thereby the above-mentioned drawbacks are overcome.

In order to achieve the object set forth above the present invention comprises a preparation of inner members by attaching absorbent cores to inner webs at predetermined spacings longitudinally of the inner webs. Each of the inner members is folded in two along its center line so that one half of the core is located on a first outer surface of the inner web and the other half is located on a second outer surface of the inner web which is opposite to said first outer surface.

On the other hand each of two continuous outer webs having a sufficient width to cover said first and second outer surfaces is provided in pre-determined areas with elastic members for leg-openings as well as waist-openings.

Said pre-determined areas of said outer members provided with said elastic members are placed on said first and second outer surfaces of said inner members to form continuous laminate.

Said continuous laminate is cut after successive sealing at pre-determined areas thereof.

The present invention makes it possible to prepare the individual inner members free from adversely effects of contracting force of the elastic members for the leg-openings and waist-openings during operation of folding, since the outer webs are provided with the elastic members for the leg-openings and waist-openings and the inner members having the inner webs and the cores are folded in two. Consequently, the previously mentioned defective features resulting in partial floating, development of wrinkles and misalignment of front and rear bodies is effectively overcome and desired neat appearance of the individual articles is acquired.

In a preferred embodiment preformed absorbent cores keep themselves from getting out their initial shapes during the operation folding of the inner members.

EMBODIMENT

Exemplary Embodiment No. 1

The present invention will be described by way of example in reference with the accompanying drawings.

Figure 1:
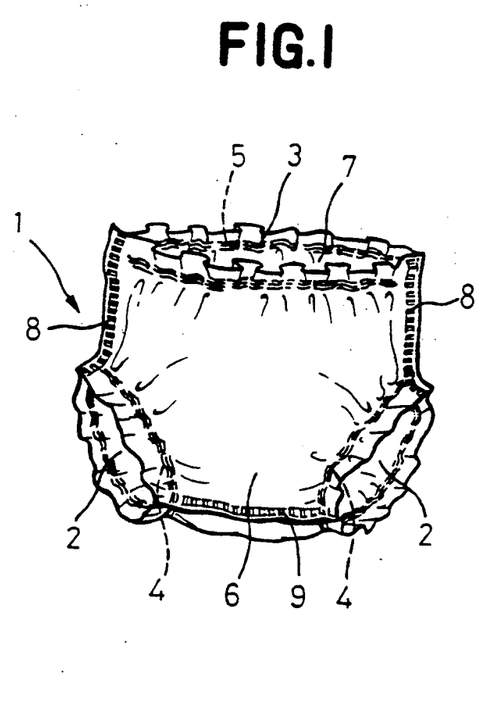
FIG. 1 is a perspective view illustrating the article manufactured by the method according to the present invention.

FIG. 1 is a perspective view illustrating a garment manufactured by the method according to the present invention.

A garment 1 comprises elastic members 4, 5 provided along leg-openings 2 and a waist-opening 3, respectively, front and rear bodies 6, 7, and heat seals or sonic seals being provided along both side edges 8 and a crotch lower edge 9 of said front and rear bodies 6, 7, respectively. As will be described in detail later, each of said front and rear bodies 6, 7 comprises inner and outer webs and an absorbent core sandwiched therebetween, and the elastic members 4, 5 are elastically bonded between said inner and outer webs by means of adhesive.

Figure 2:
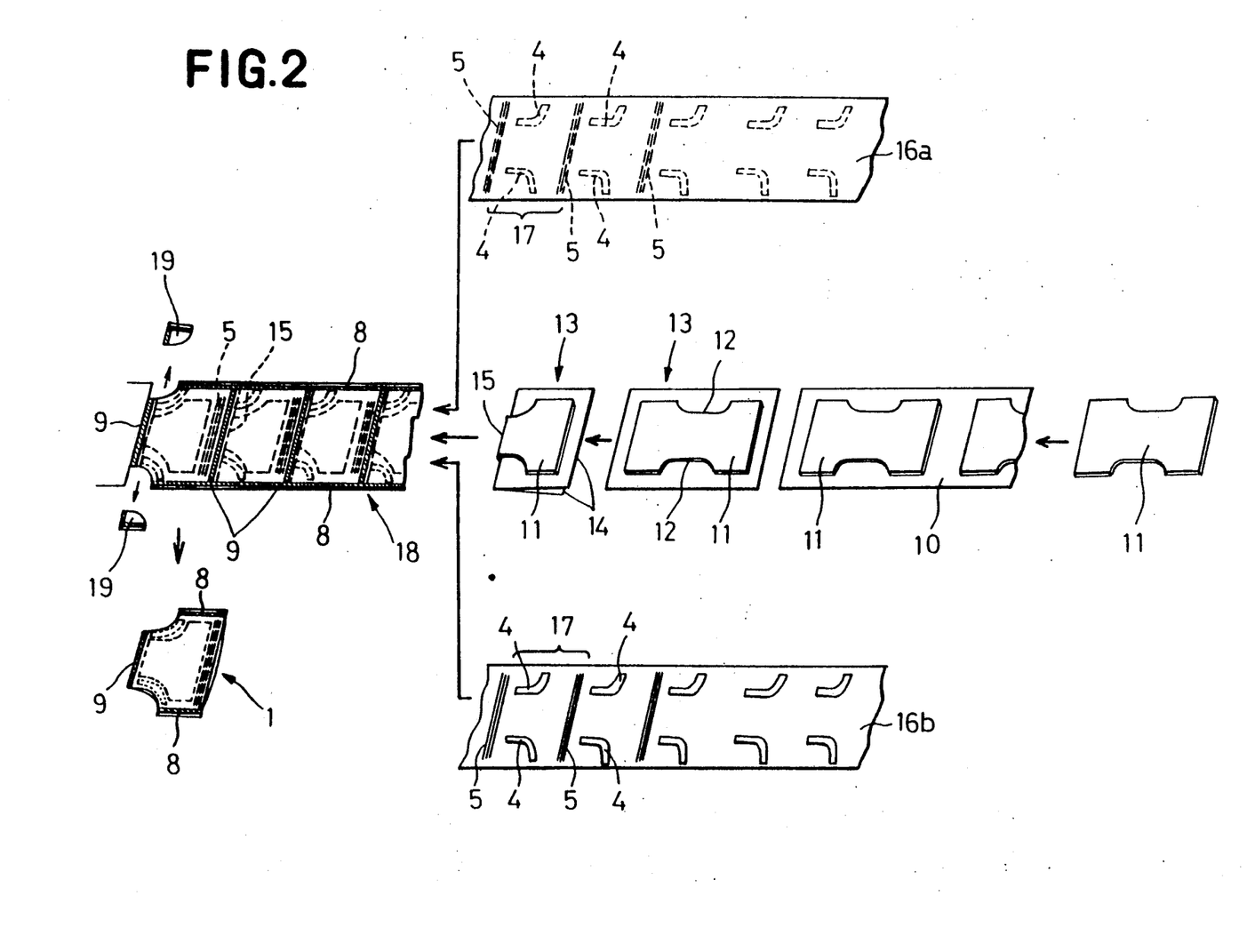
FIG. 2 is a schematic perspective view sequentially illustrating how the method is implemented in Exemplary Embodiment No. 1 of the present invention.

FIG. 2 is a schematic perspective view sequentially illustrating how the method is implemented in the present invention.

Moving a continuous inner web 10 of nonwoven fabric being elastic both in length and width (i.e., biaxially elastic) and having a given width to an assembly line (not shown), respective absorbent cores 11 each having a width narrower than the width of said inner web and preformed in an hourglass-shape are immovably attached to top surface of said inner web along transversely middle zone by means of hot melt type adhesive (not shown) so that the respective cores 11 have their lengths oriented transversely of said inner web and are successively spaced from one another by a given distance longitudinally of said inner web.

The core 11 is made from a substantially homogeneous mixture of fluffy pulp, crimped thermoplastic staple fibers and super-absorptive polymer particles. Specifically, this mixture is subjected to heat treatment to bond said staple fibers each other and, after sprayed with appropriate amount of water, compressed with appropriate pressure in the direction of thickness thereof to form a continuous web from which the individual sheet- or mat-like cores are cut out. The individual core 11 thus cut out is hourglass-shaped, i.e., provided along each side with arcuate cut-in 12, respectively, so as to define a constricted middle portion. The core 11 will not easily get out of its initial shape.

The continuous inner web 10 is successively cut off along the transverse direction between adjacent cores 11 to form inner members 13. The inner member 13 formed in such a manner as has been described above is then successively folded along a transverse center line 15 so that one half of each core 11 is located on top side (first outer surface) and the other half of this core 11 is located on bottom side (second outer surface) and longitudinally opposite edges 14 of said inner web lie substantially on a same line as the inner member 13 is moved to the assembly line.

Simultaneously, a pair of continuous outer webs 16a, 16b are moved to the assembly line. Each of said outer webs has a width corresponding to the width of the continuous inner web 10 and comprises nonwoven fabric which is biaxially elastic, the nonwoven fabric whose inside is lined with biaxially elastic plastic film under intermittent bonding, or the plastic film alone. Each inside of these outer webs 16a, 16b is provided with symmetrically paired elastic members 4 for the leg-openings, which are bonded on both sides of respective given areas 17 corresponding to the respective sizes of top and bottom surfaces of respective inner members 13 by means of hot melt type adhesive (not shown) under arcuately curved and stretched condition. The elastic member 4 for the leg-opening is preferably curved along substantially a half of each cut-in 12 of the core 11. Further, there are provided elastic members 5 for waistopenings each transversely extending within said given areas 17 of the outer webs 16a, 16b between pairs of the symmetrically paired elastic members 4 being adjacent to each other longitudinally of the outer webs 16a, 16b. These elastic members 5 are linear and attached by means of hot melt type adhesive (not shown) under stretched condition.

These outer webs 16a, 16b are attached to top and bottom surfaces of the aligned inner member 13 so that the given areas 17 coincide with said surfaces of inner member 13 and thereby a continuous laminate 18 is formed.

The laminate 18 is heat- or sonic-sealed along both longitudinal side edges thereof by means of sealing line 8, and heat- or sonic-sealed transversely between transverse fold 15 of the inner member 13 and the elastic member 5 for the waist-opening by means of sealing line 9.

Finally, the laminate 18 is successively cut along the transverse (imaginary) lines assumed between the elastic member 5 for the waist-opening and the transverse sealing line 9 which is adjacent the elastic member 5, and portions 19 extending outside the elastic members 4 for the leg-openings are successively cut away to form individual articles 1 (See FIG. 1).

Exemplary Embodiment No. 2

Figure 3:
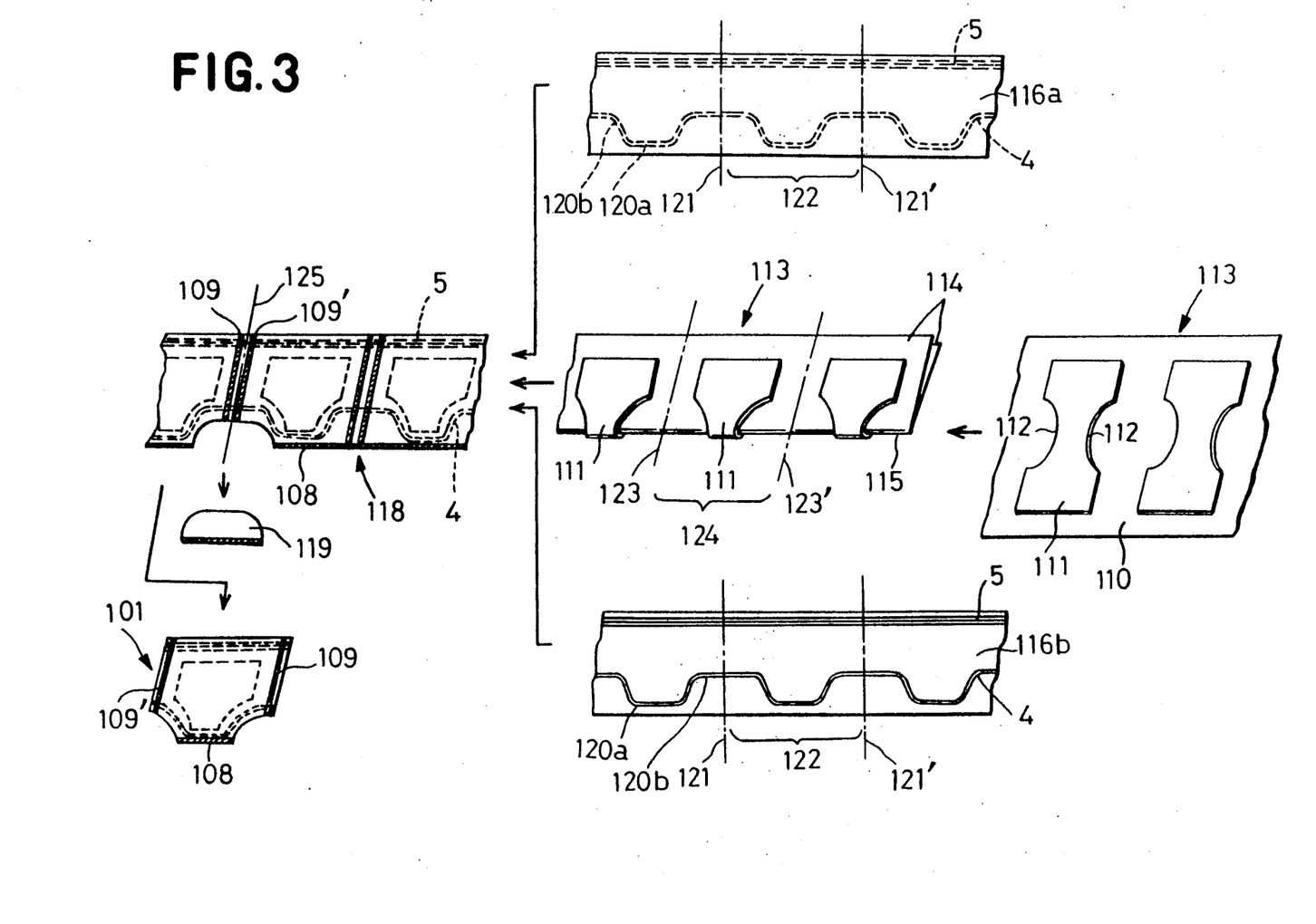
FIG. 3 is a schematic perspective view illustrating the method in Exemplary Embodiment No. 2 of the present invention.

FIG. 3 is a schematic perspective view sequentially illustrating how the method of the present invention is implemented.

Moving a continuous inner web 110 made of nonwoven fabric being elastic both in length and width (biaxially elastic) and having a width corresponding to a length of each finished product to an assembly line (not shown), respective absorbent cores 111 each having a length smaller than the width of inner web and preformed in an hourglass-shape are immovably attached to top surface of said inner web in its transversely middle zone by means of hot melt type adhesive (not shown) so that the respective cores 111 have their lengths oriented transversely of said inner web and are successively spaced from one another longitudinally of said inner web so as to form an inner members 113.

The core 111 is the same one as core 11 used in Exemplary Embodiment No. 1.

The inner members 113 formed in the manner as has been described above is then successively folded along a transverse center line 115 so that one half of each core 111 is located on top side (first outer surface) and the other half of this core 111 is located on bottom side (second outer surface) and longitudinally opposite edges 114 of said inner web lie substantially on a same line as the inner members 113 are moved to the assembly line.

Simultaneously, a pair of continuous outer webs 116a, 116b are moved to the assembly line. Each of said outer webs has a width which is slightly larger than the width of top side (first outer surface) and bottom side (second outer surface) of each folded and aligned inner member 113, and comprises nonwoven fabric being biaxially elastic, laminate sheet consisting of the nonwoven fabric intermittently bonded with plastic film being biaxially elastic, or the plastic film alone. Each inside of these outer webs 116a, 116b is provided along and adjacent one side edge (first side edge) with zigzag elastic members 4 for the leg-openings and along the opposite side edge (second side edge) with linear elastic members 5 for the waist-opening. These elastic members 4, 5 are attached by means of hot melt type adhesive (not shown) under their stretched condition. The zigzag configuration of the elastic members 4 for the leg-openings is such that troughs 120a and swellings 120b alternate longitudinally of the outer webs 116a, 116b. Each trough 120a finds itself at longitudinally middle position of each area 122 defined by transverse (imaginary) defining lines 121, 121' assumed at given spacings longitudinally of the outer web 116a, 116b. Each area 122 has a same size as an area 124 on the inner member 113 defined by transverse (imaginary) defining lines 123, 123' spaced from one another by a given distance longitudinally of said inner member 113 and the core 111 is positioned thereon at the middle location longitudinally of said area 124. Curved portions of the elastic members 4 for the leg-openings preferably extend substantially along longitudinally one half of each arcuate cut-in 112 of the core 111.

These outer webs 116a, 116b are placed on top and bottom surfaces of inner members 113 on an assembly line so that outer webs 116a, 116b coincide with corresponding areas 122, 124 each other and thereby a continuous laminate 118 is formed.

The laminate 118 is provided with heat- or sonic-sealings 108, 109, 109', respectively, along said first side edge, i.e., the one side edge adjacent the elastic members 4 for the leg-openings and along transverse (imaginary) lines extending symmetrically with respect to the respective transverse defining lines 121, 121'.

Finally, the laminate 118 is successively cut along the transverse (imaginary) lines 125 assumed between respective adjacent heat- or sonic-sealings 109, 109', and areas 119 extending outside the elastic members 4 for the leg-openings are successively cut away to form individual articles 101 (See FIG. 1).

It should be understood that though any embodiment of the apparatus used to implement the method of the present invention is neither illustrated nor described, the method can be realized by suitable apparatus of prior arts.

Exemplary Embodiment No. 3

Figure 4:
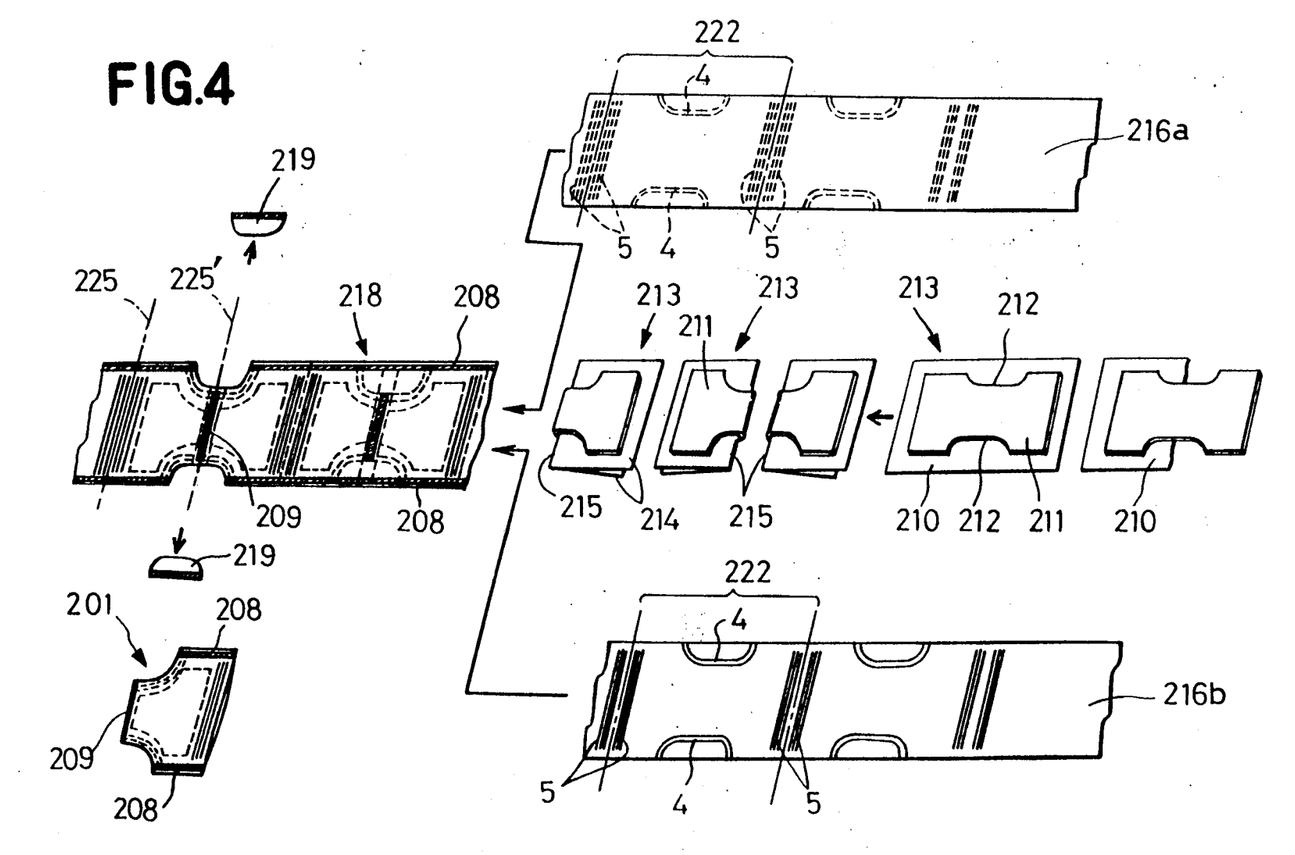
FIG. 4 is a schematic perspective view illustrating the method in Exemplary Embodiment No. 3 of the present invention.

In FIG. 4, moving a continuous inner web 210 made of nonwoven fabric being biaxially elastic and having a given width to an assembly line (not shown), respective absorbent cores 211 each having a width narrower than the width of said inner web 210 and preformed in an hourglass-shape are immovably attached centrally to top surface of the inner web 210 by means of hot melt type adhesive (not shown) so that the respective cores 211 are successively spaced from one another by a given distance longitudinally of the inner web 210.

The core 211 is the same one as core 11 used in Exemplary Embodiment No. 1.

The continuous inner web 210 is successively cut in the transverse direction between the adjacent cores 211 to form individual inner members 213. Each of the inner members 213 formed in the manner as has been described above is then folded in two along a longitudinal center line 215 so that one half of each core 211 is located on top side (first outer surface), the other half of this core 211 is located on bottom side (second outer surface) and longitudinally opposite ends 214 of said inner web lie substantially on a same line. The respective inner members 213 each folded on itself are moved in series to the assembly line with the folds (transversely center lines) 215 of each pair of the adjacent inner members 213 in said series being closely opposed to or in contact with each other.

Simultaneously, a pair of continuous outer webs 216a, 216b are moved to the assembly line. Each of said outer webs 216a, 216b has a width corresponding to the width of the continuous inner web 210 and comprises nonwoven fabric being biaxially elastic, laminate sheet consisting of the nonwoven fabric intermittently bonded with plastic film being biaxially elastic, or the plastic film alone. Each inside of these outer webs 216a, 216b is provided with symmetrically paired elastic members 4 for the leg-openings attached to both sides of respective given areas 222 corresponding to twice the respective sizes of top and bottom surfaces of the respective inner members 213 by means of hot melt type adhesive (not shown) under arcuately curved and stretched condition. Each elastic member 4 for the leg-opening is preferably curved along substantially each cut-in 212 of the core 211. Further, there are provided two groups of elastic members 5 for the waist-opening each transversely extending within said given area 222 of the outer webs 216a, 216b between pairs of symmetrically paired elastic members 4 being opposed to each longitudinally of said outer webs 216a, 216b. These groups of elastic members 5 are linear and attached to the outer webs 216a, 216b by means of hot melt type adhesive (not shown) under stretched condition.

These outer webs 216a, 216b are attached to top and bottom surfaces of the inner members 213 being moved in series so that the areas 222 of the webs 216a, 216b well coincide with the top and bottom surfaces of the respective inner members 213 and thereby a continuous laminate 218 is formed.

The laminate 218 is sealed by heat- or sonic-sealings 208, 209 along both longitudinal side edges thereof and along respective transverse (imaginary) lines extending between the opposed transverse folds 215 of the adjacent inner members 213, respectively.

Finally, the laminate 218 is successively cut along the transverse lines 225 assumed between paired elastic members 5 for the waist-openings and along assumed center lines 225' of transverse heat- or sonic-sealings 209. Then, portions 219 extending outside the elastic members 4 for the leg-openings are successively cut away to form individual articles 201 (See FIG. 1).

Exemplary Embodiment No. 4

Figure 5:
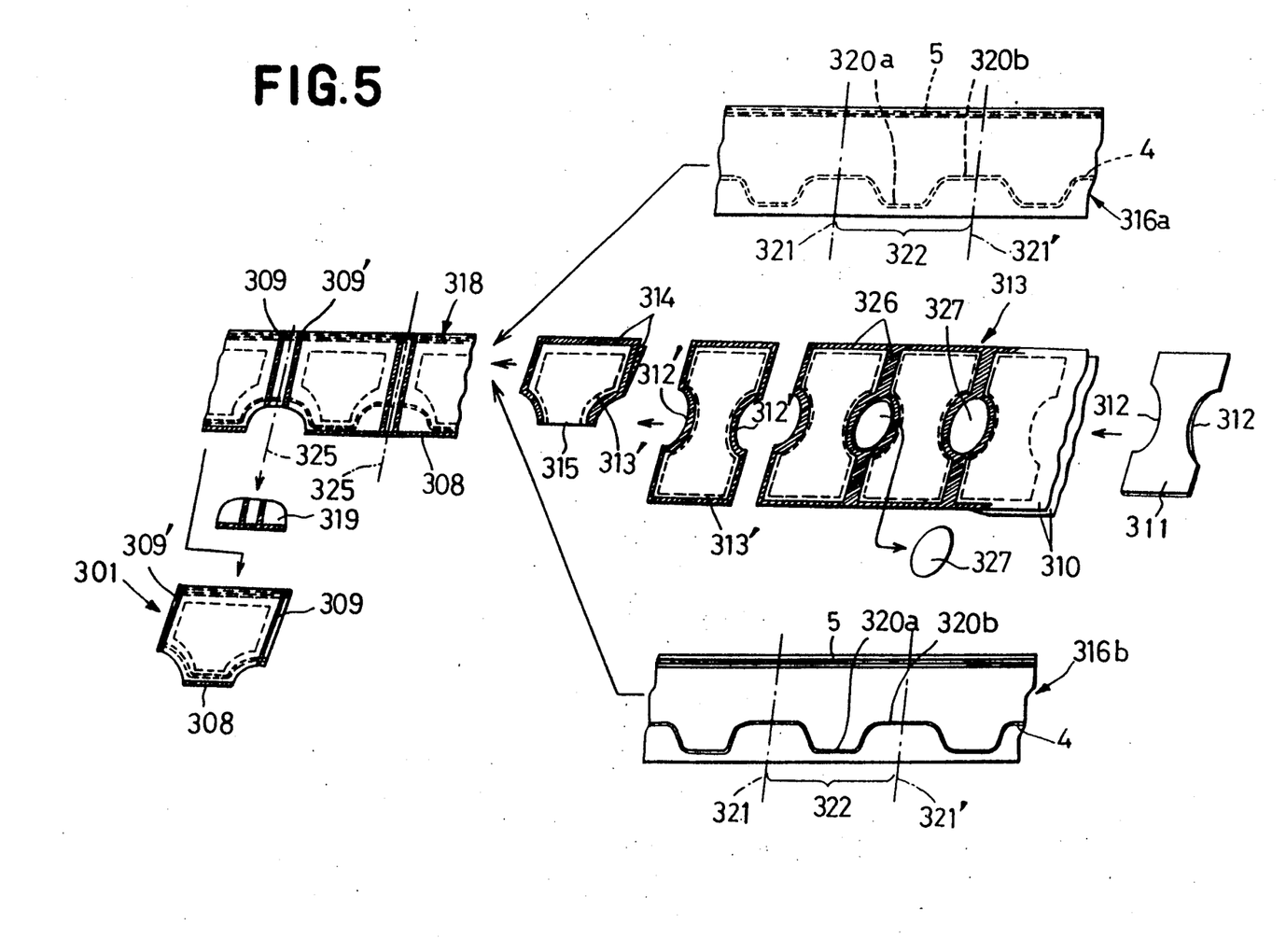
FIG. 5 is a schematic perspective view illustrating the method in Exemplary Embodiment No. 4 of the present invention.

In FIG. 5, moving a pair of continuous inner webs 310 made of tissue-paper or nonwoven fabric and having a width corresponding to a length of each finished product to an assembly line (not shown), respective absorbent cores 311 each having a length substantially corresponding to the width of said inner webs and preformed in an hourglass-shape are immovably placed between said inner webs by means of hot melt type adhesive (not shown) so that the respective cores 311 have their lengths oriented transversely of the inner webs and are successively spaced from one another longitudinally of the inner webs. The pair of inner webs 310 are bonded together by hot melt type adhesive (not shown) or welding along peripheral edges of the respective cores 311 to form a continuous inner member 313. In this manner, this continuous inner member 313 is provided with bonded area 326 and central elliptic areas 327.

The core 311 is the same one as core 11 used in Exemplary Embodiment No. 1.

The continuous inner member 313 containing the cores 311 is then transversely cut along respective center (imaginary) lines on sections of the bonded area 326 extending between the respective pairs of adjacent cores 311 to form unit inner members 313' each having arcuate cut-in 312' along each side so as to define an hourglass-shape.

Each unit inner member 313' is longitudinally folded in two with its longitudinal opposite ends 314 coming substantially on a same line.

These unit inner members 313' are then moved successively with side by side alignment with their ends 315 corresponding to their folds lying on a same line and their transverse side edges being in contact with or closely adjacent to one another as they are moved to the assembly line.

Simultaneously, a pair of continuous outer webs 316a, 316b are moved to the assembly line. Each of said outer webs has a width slightly larger than the length of top (first outer surface) or bottom (second outer surface) of the unit inner members 313' which have been folded up and arranged side by side, and comprises nonwoven fabric being biaxially elastic, laminate sheet consisting of the nonwoven fabric intermittently bonded with plastic film being biaxially elastic, or the film alone. Each inside of these outer webs 316a, 316b is provided along and adjacent one side edge (first side edge) with zigzag elastic members 4 for the leg openings and along the opposite side edge (second side edge) with linear elastic members 5 for the waist-openings. These elastic members 4, 5 are attached by means of hot melt type adhesive (not shown) under their stretched condition. The zigzag configuration of the elastic members 4 for the leg openings is such that troughs 320a and swellings 320b alternate longitudinally of the outer web 316a, 316b and each trough 320a finds itself at longitudinally middle position of each area 322 defined by transverse (imaginary) defining lines 321, 321' assumed at given spacings longitudinally of the outer web 316a, 316b.

These outer webs 316a, 316b are attached to moving unit inner members 313' so that both the first and second outer surfaces of said unit inner members 313' are completely covered by area 322, and thereby a continuous laminate 318 is formed. In this laminated condition, the core 311 is located at the center of each area 322. The undulating configuration of the elastic member 4 contains the swellings preferably extending substantially along each arcuate cut-in 312' of each unit inner member 313'.

The laminate 318 is provided along the first side edge, i.e., the one side edge adjacent the elastic member 4 for the leg-openings and along transverse (imaginary) lines extending symmetrically with respect to the respective transverse defining lines 321, 321' with heat- or sonic-sealings 308, 309, 309', respectively. If necessary, the outer web 316a and the first outer surface of the respective unit inner members 313' may be attached to each other, and the outer web 316b and the second outer surface of the respective inner members 313' may be attached to each other, by means of heat-sealing or adhesive. It should be understood that, depending on the curing or hardening condition of a specific adhesive applied to attach the elastic member 5 to the outer webs 316a, 316b, this applied adhesive may be additionally utilized to attach the outer webs 316a, 316b to said first and second outer surfaces of the unit inner members, respectively.

Finally, the laminate 318 is successively cut along the transverse (imaginary) lines assumed between adjacent heat or sonic-sealings 309, 309', i.e., the transverse defining lines 325, and areas 319 extending outside the elastic member 4 for the leg-openings are successively cut away to form individual articles 301 (See FIG. 1).

It should be understood that though in any exemplary embodiment the apparatus used to implement the method of the invention is neither illustrated nor described, the method can be realized by suitable apparatus of prior arts.

What is claimed is:

1. Method for manufacturing disposable garments comprising steps of:
    attaching respective absorbent cores to a continuous inner web so that said cores are successively spaced from one another by a predetermined distance longitudinally of said inner web to form inner members;
    folding said inner members along their middle zone so that each of said core is located on first and second outer surfaces of said inner members;
    providing predetermined areas of a pair of continuous outer webs having widths substantially corresponding to respective said first and second outer surfaces of said inner members with elastic members for leg-openings and waistopenings;
    attaching said respective predetermined areas of said outer webs provided with said elastic members to said respective first and second outer surfaces of said inner members to form a continuous laminate;
    sealing respective predetermined areas of said continuous laminate; and
    cutting respective predetermined areas of said continuous laminate to form individual disposable garments.

2. Method for manufacturing disposable garments comprising steps of;
    attaching respective absorbent cores each having a width smaller than a width of a continuous inner web to said continuous inner web so that said respective cores are successively spaced from one another by a predetermined distance longitudinally of said inner web, successively cutting said inner web transversely along a center line assumed between said adjacent scores to define an individual inner member, and thereafter folding each of said inner member in two longitudinally thereof with their cores located on first and second outer surfaces of said inner member and their longitudinally opposite ends of said inner web lying substantially on a same line, and arranging said respective folded inner members side by side with their transverse edges, i.e. folds created by said folding being in contact or closely adjacent to longitudinally opposite ends thereof in the neighboring inner members;
    providing each inside of a pair of continuous outer webs each having a width substantially corresponding to a width of said inner web with symmetrically paired elastic members for leg-openings longitudinally on both sides of respective given areas corresponding to the respective sizes of said first and second outer surfaces of said inner members, and with elastic members for waist-openings each transversely extending within said respective given areas of said outer webs between pairs of said symmetrically paired elastic members for the leg-openings adjacent to each other longitudinally of said outer webs;
    attaching said outer webs to said first and second outer surfaces of said inner members, respectively, with given areas on said respective outer webs coinciding with said first and second outer surfaces of said inner member so as to form a continuous laminate;
    sealing said continuous laminate along longitudinal side edges thereof, and between said transverse edges of said inner members created by folding and said elastic members for said waist-opening;
    cutting said laminate transversely thereof between said elastic members for said waist-openings and transverse sealing lines created by said sealing, and cutting away areas extending outside said elastic member for said leg-openings to form individual finished articles.

3. Method for manufacturing disposable garments comprising steps of:
    attaching respective absorbent cores each having a length smaller than a width of a continuous inner web, said width in turn corresponding to a length of each finished article to said continuous inner web intermittently in transversely middle zone so that said respective cores have their length oriented transversely of said inner web and are successively spaced from one another by a predetermined distance longitudinally of said inner web to form a continuous inner member and thereafter transversely folding said inner member so that each of said cores is located on first and second outer surfaces of said inner member and transversely opposite ends of said inner web lie substantially on a same line;

providing each inside of a pair of continuous outer webs each having a width substantially corresponding to a length of said first outer surface or said second outer surface of said inner member along and adjacent a first side edge with continuous elastic members for leg-openings and along a second side edge with continuous elastic members for waist-openings;

attaching said outer webs to said first and second outer surfaces of said inner members, respectively, with given areas of said respective outer webs coinciding with said given areas of said first and second outer surfaces of said inner member so as to form a continuous laminate;

heat- or sonic-sealing said continuous laminate along one side edge extending along said first side edge and along narrow zones extending symmetrically with respect to transverse center lines defining each of said given areas; and cutting said laminate transversely thereof, leaving respective transverse seals created by said sealing on respective longitudinally adjacent articles to be finished and cutting away areas extending outside said elastic members for said leg-openings to form individual finished articles.

4. Method for manufacturing disposable garments comprising steps of:

attaching absorbent cores each having a width narrower than a width of a continuous inner web to said continuous inner web at given spacings longitudinally thereof with lengths of the respective cores being oriented longitudinally of said continuous inner web, then successively cutting said inner web along central (imaginary) lines of respective transverse zones separating the respective cores to form individual inner members each of which is then folded up in its longitudinal direction so that the associated core is partially located on a first outer surface and partially located on a second outer surface opposed to said first outer surface of said inner member and longitudinally opposite ends of said inner member lie substantially on a same line, and aligning the respective inner members so that the ends of the respective inner members corresponding to folds created by said folding are in contact with or closely adjacent to the ends corresponding to the folds of the respectively neighboring inner members corresponding to the folds;

providing each inside of a pair of continuous outer webs each having a width substantially corresponding to the width of said inner web with symmetrically paired elastic member for leg-openings so that each paired elastic member extends along both sides of a given area corresponding to twice the respective sizes of said first and second surfaces of said inner member and said respective paired elastic members are spaced from one another by a given distance longitudinally of the respective inner members and further with elastic members for waist-opening each transversely extending within said given area between pairs of said symmetrically paired elastic members adjacent longitudinally of said outer web;

attaching said outer webs to said aligned inner members with the respective given areas coinciding with said first and second outer surfaces of said inner members to form a continuous laminate;

sealing said laminate along both longitudinal side edges thereof and along respective transverse (imaginary) center lines between said opposite transverse folds of said inner members; and transversely cutting said laminate between said adjacent elastic members for said waist-openings and along transverse (imaginary) center lines of seals created by said transverse sealing, and cutting away portions extending outside said elastic members for said leg-openings to form individual articles.

5. Method for manufacturing disposable garments comprising steps of:

arranging respective absorbent cores each having a length not larger than a width of a pair of continuous inner webs, said width in turn corresponding to a length of each finished product, between said pair of continuous inner webs so that the respective cores have their lengths oriented transversely of said inner webs and are successively spaced from one another by a predetermined distance longitudinally of said inner webs and thereafter bonding said pair of inner webs together along peripheral edges of said respective cores to form a continuous inner member;

transversely cutting said continuous inner member along respective (imaginary) lines on sections of bonded area extending between the respective adjacent cores to form unit inner members;

folding said unit inner members in two longitudinally thereof with their longitudinally opposite ends lying on a same line and their ends corresponding to their folds created by said folding lying on a same line and arranging them side by side with their transverse side edges being in contact with or closely adjacent to one another;

providing each inside of a pair of continuous outer webs each having a width substantially corresponding to the length of first or second outer surface of said unit inner members having been folded and arranged side by side along and adjacent a first side edge with continuous elastic members for leg-openings and along a second side edge with continuous elastic members for waist-openings;

attaching said outer webs to said first and second outer surfaces of said unit inner members, respectively, with given areas of said respective outer webs coinciding with given areas on said first and second outer surfaces of the corresponding unit inner members to form a continuous laminate;

sealing said laminate along one side edge extending along said first side edge and along (imaginary) transverse lines extending symmetrically with respect to said transverse center lines defining said given areas respectively; and cutting said laminate transversely thereof, leaving said each transverse seal created by said sealing on each of longitudinally adjacent articles to be finished and cutting away areas extending outside said elastic members for said leg-openings from said pair of adjacent articles to form individual finished articles.

6. Method as recited in any one of claims 1 to 5, wherein said core is preformed into a mat or a sheet from a mixture of fluffy pulp, staple fibers and absorptive polymer particles.

* * * * *